United States Patent
Lesage et al.

(10) Patent No.: US 8,235,525 B2
(45) Date of Patent: Aug. 7, 2012

(54) METHOD FOR MAKING AN ASPHERIC INTRAOCULAR LENS

(75) Inventors: Cédric Lesage, Sainte-Soulle (FR); Mario Gerlach, Altenberga (DE)

(73) Assignee: Carl Zeiss Meditec AG, Jena (DE)

( * ) Notice: Subject to any disclaimer, the term of this patent is extended or adjusted under 35 U.S.C. 154(b) by 0 days.

(21) Appl. No.: 13/064,073

(22) Filed: Mar. 4, 2011

(65) Prior Publication Data

US 2011/0157548 A1 Jun. 30, 2011

Related U.S. Application Data

(60) Division of application No. 12/289,789, filed on Nov. 4, 2008, now abandoned, which is a continuation of application No. PCT/EP2007/003674, filed on Apr. 26, 2007.

(30) Foreign Application Priority Data

May 5, 2006 (DE) .......................... 10 2006 021 521

(51) Int. Cl.
G02C 7/02 (2006.01)
(52) U.S. Cl. ...................................... 351/177; 623/6.11
(58) Field of Classification Search ................ 351/177, 351/246; 623/4.1, 6.11–6.24
See application file for complete search history.

(56) References Cited

U.S. PATENT DOCUMENTS

| | | | |
|---|---|---|---|
| 5,530,491 A | 6/1996 | Baude et al. | 351/169 |
| 5,560,491 A * | 10/1996 | Romaniuk et al. | 206/573 |
| 5,760,871 A | 6/1998 | Kosoburd et al. | 623/6.3 |
| 6,126,286 A | 10/2000 | Portney | |
| 6,609,793 B2 * | 8/2003 | Norrby et al. | 351/212 |
| 6,923,539 B2 | 8/2005 | Simpson et al. | |
| 7,137,702 B2 | 11/2006 | Piers et al. | |
| 7,241,311 B2 | 7/2007 | Norrby et al. | |
| 7,377,641 B2 | 5/2008 | Piers et al. | |
| 2005/0203619 A1 | 9/2005 | Altmann | |
| 2006/0030938 A1 | 2/2006 | Altmann | |

FOREIGN PATENT DOCUMENTS

| | | |
|---|---|---|
| EP | 1 003 446 | 5/2000 |
| EP | 1 402 852 | 3/2004 |
| WO | WO 2005/046527 | 5/2005 |

OTHER PUBLICATIONS

Nio et al, "Spherical and irregular aberrations are important for the optimal performance of the human eye", Ophthal. Physiol. Opt., 2002, 22, The College of Optometrists, pp. 103 to 112.

(Continued)

*Primary Examiner* — James Greece
(74) *Attorney, Agent, or Firm* — Walter Ottesen

(57) ABSTRACT

The invention relates to a novel artificial intraocular lens (IOL) and a method for improving such a lens in the field of ophthalmology, with surface shape modifications that differ from perfect spherical geometries. The intraocular lens takes into account the natural optical configuration of the human vision apparatus, for example, visual axis tilt and pupil decentration. In addition, the method accounts for potential positioning errors caused by implantation and surgery effects.

14 Claims, 7 Drawing Sheets

OTHER PUBLICATIONS

Artal et al, "Neural compensation for the eye's optical aberrations", Journal of Vision, 2004, 4, ARVO, pp. 281 to 287.

Southall, ed., "Helmholtz's Treatise on Physiological Optics", 1924, vol. 1, The Optical Society of America, pp. xxi, 350 to 358.

Liou et al, "Anatomically accurate, finite model eye for optical modeling", J. Opt. Soc. Am., Aug. 1997, A/vol. 14, No. 8, Optical Society of America, pp. 1684 to 1695.

Taketani et al, "Influence of intraocular lens optical design on high-order aberrations", J Cataract Refract Surg, 2005, 31, Elsevier Inc., pp. 969 to 972.

Noll, R., "Zernike polynomials and atmospheric turbulence", J. Opt. Soc. Am., Mar. 1976, vol. 66, No. 3, Optical Society of America, pp. 207 to 211.

Taketani et al, "Influence of intraocular lens tilt and decentration on wavefront aberrations", J Cataract Refract Surg, 2004, 30, Elsevier Inc., pp. 2158 to 2162.

Kasper et al, "Intraindividual comparison of higher-order aberrations after implantation of aspherical and spherical intraocular lenses as a function of pupil diameter", J Cataract Refract Surg, 2006, 32, Elsevier Inc., pp. 78 to 84.

Ye et al, "A New Single-Surface Model Eye That Accurately Predicts Chromatic and Spherical Aberrations of the Human Eye", Abstract, Applied Optics, 1992, pp. 3594 to 3600, vol. 31.

Born et al, "Principles of Optics, Electromagnetic theory of propagation, interference and diffraction of light", Seventh (Expanded) Edition, 1999, pp. 517 to 553, Cambridge University Press.

* cited by examiner

METHOD FOR MAKING AN ASPHERIC INTRAOCULAR LENS

CROSS REFERENCE TO RELATED APPLICATIONS

This application is a divisional application of U.S. patent application Ser. No. 12/289,789, filed Nov. 4, 2008 now abandoned, which, in turn, is a continuation application of international patent application PCT/EP 2007/003674, filed Apr. 26, 2007, designating the United States and claiming priority from German application 10 2006 021 521.4, filed May 5, 2006, and the entire content of all of the above applications is incorporated herein by reference.

FIELD OF THE INVENTION

The invention relates to a novel intraocular lens (IOL) and a method for improving such a lens in the field of ophthalmology, including modifications of the surface shape that differ from a perfect spherical geometry.

BACKGROUND OF THE INVENTION

The treatment of cataract, as the world's most common cause for blindness, is a well known process since the time of ancient Rome (first and second century AD). Since that time, the complete removal of the opaque human lens is still the best choice to partially restore visual acuity of the patient. The achieved results are unexpectedly poor because of the disregarded refractive contributions of the natural human lens to the visual apparatus which are not adequately compensated in this situation.

A breakthrough in cataract surgery was made in 1949 when the English physician Harold Ridley successfully implanted the first intraocular lens made of hard PMMA plastics. This lens was capable to compensate for lost optical power of the natural human lens. Since this time IOLs and surgical techniques were continuously improved. Today cataract surgery is by far the most performed surgery in ophthalmology with more than 2.3 million patients per year in the United States and approximately another 3 million surgeries in Europe and Japan.

The capacity of the human eye as an optical system can only be accomplished if the artificial lens is properly positioned and focused. If this condition is satisfied, the incident rays from distant object points form only minimally blurred spots at the retina and provide sharp vision. The correct adaptation of an IOL to the individual human eye remains difficult and the postoperative visual acuity of the patient depends on several factors.

Inaccuracies during measurement of the various ocular geometries, inaccuracies during surgery and postsurgical effects (such as surgical trauma and wound healing processes) limit the achievable visual acuity due to positioning errors of the implanted IOL. Positioning errors with respect to the optical axis mainly cause defocusing while tilt and decentration of the IOL will result in induced astigmatism and coma errors. Higher-order optical aberrations will appear as well.

Up to the present time, different IOL design approaches deal with these problems and try to mitigate the problems with particular emphasis on certain aspects.

A selection of prior art lens designs is described in brief hereinafter.

The equi-convex lens design (example Bausch & Lomb LI61U) is the most used intraocular lens design in clinical practice. Both lens surfaces are spherical with equivalent radii of curvature. As a consequence, these designs produce a significant amount of spherical aberration. Due to the strong increase of spherical aberration with increasing pupil diameter, the patients will very likely suffer from blurry vision and contrast loss under mesopic/scotopic conditions.

The biconvex or plano-convex lens (example AMO sensar AR40) is another lens design. The additional degrees of freedom allow designing a "best shaped IOL" that provides minimal spherical aberration that is achievable with spherical surfaces. The amount of spherical aberration is significantly reduced as compared with the above lens. Since the amount of spherical aberration (SA) is still higher than with the natural human lens, the patient will very likely suffer from blurry vision and contrast loss under mesopic/scotopic conditions due to spherical aberration.

A wavefront optimized IOL (example Pharmacia, TECNIS 29000) is described in U.S. Pat. No. 6,609,793 B2. The anterior surface is aspherical. The deviations from the base sphere are expressed as a sixth order polynomial expansion. The IOL design is based on averaged wavefront aberrometry data obtained on a large patient cohort. The objective of the aspherization is to compensate for the positive spherical aberration as induced by the normal human cornea. The IOL has to provide a certain amount of negative spherical aberration to bring the entire optical apparatus to zero spherical aberration. As viewed from a theoretical optics perspective, this design should provide maximum optical performance at the narrowest possible point spread function. The lens TECNIS 29000 provides a diffraction limited optical performance in the axis-near region. This holds true even for large pupil diameters of 6 mm. Such lens design, however, has also some disadvantages. Due to the intended significant negative spherical aberration of the lens, the latter becomes very sensitive with respect to decentration that is likely to occur during the implantation and after implantation during capsular bag symphysis. The diffraction limited performance of the lens vanishes immediately even if slightly decentered.

The "aberration-free IOL" (example Bausch and Lomb, SofPort A0 and Akreos AO) is disclosed in United States patent publication US 2005/203619 A1 and WO 2004/090611 A3. Both surfaces of the IOL are aspherical and the shape is defined by a conic constant. Considering the specific optical conditions behind the cornea, the IOL does not introduce any additional spherical aberration into the optical system. In other words, the IOL is "transparent" for the incoming aberrations. Systems that do not introduce spherical aberrations do not introduce coma while decentered. Therefore, these lenses can be significantly decentered without losing contrast when compared to the perfectly centered state. Since the spherical aberration of the cornea is not affected by the IOL, this amount of spherical aberration is manifest and limits the optical performance in the axial region. The "aberration-free IOL" does not correspond to the physiological properties of the natural human lens and therefore can lead to sub-optimal results. This lens can be used for eyes after refractive surgery, eyes with keratoconus or with atypical corneal spherical aberration.

There are several other patent publications directed to the subject of increasing the spherical aberrations in order to provide depth of field or achieve pseudoaccommodation.

In United States patent publication US 2004/0230299 (Nov. 18, 2005), an oscillating surface superimposed on a spherical surface is provided to produce different focus points forward and rearward of the best focus in order to obtain an increased depth of focus.

Patent publication WO 2005/046527 (May 26, 2005) discloses a multizone monofocal lens. Each zone presents a positive or negative gradient of refractive power proceeding from the base power of the lens in order to produce an extended depth of field.

U.S. Pat. No. 6,126,286 (Oct. 3, 2000) discloses a multi-zone monofocal lens to produce an improved depth of field.

European patent publication 1 402 852 (Sep. 29, 2003) discloses a monofocal aspherical lens which permits a pseudoaccommodation by providing an improved depth of field (by increasing the amount of spherical aberrations).

SUMMARY OF THE INVENTION

It is an object of the invention to overcome the disadvantages of the prior art and to provide significantly improved perceivable optical performance for patients who need an IOL implant.

The invention provides a new aspheric intraocular lens and a method for making such an IOL that results in obtaining an intraocular lens which provides significantly improved perceivable optical performance to IOL patients.

The aspherical intraocular lens according to the invention has an anterior and a posterior surface and at least one of the two surfaces is aspheric. The optical properties of these surfaces account for a spherical aberration equal to or approaching the spherical aberration of the human eye.

In another embodiment of the invention, the IOL can be made of a material that has a varying refractive index so that a spherical aberration results equal to or approaching the spherical aberration of the human eye.

The invention also relates to a method for making an intraocular lens which can be adjusted to the aberrations of the eye to provide an optimal vision correction for the patient. The method includes the following steps: providing a mathematical model eye that describes the optical setup and the performance of the natural human eye including at least one aspherical corneal surface, a gradient index and/or an aspherical model of the natural eye lens, a visual axis that is tilted with respect to the "optical axis of symmetry" of the eye and a decentered iris diaphragm that represents a decentered entrance pupil; determining the performances of the mathematical model eye in terms of image quality and spherical aberrations as a function of the pupil diameter; using a mathematical model describing the statistics of potential lens misalignments and positioning errors induced by surgery or wound healing processes; calculating the optical performance and resulting aberrations with the aid of the mathematical eye model convoluted with the statistical model for lens displacements; and, optically modeling an aspherical lens shape that replaces the natural human lens in the eye and corrects for spherical vision errors while preserving specific optical properties of the human lens in order to cause the pseudophakic eye to have the same amount of spherical aberrations as a function of the pupil diameter and the same level of image quality as the phakic model eye.

In such a method either of the anterior or the posterior or both surfaces of the lens can be of aspherical shape.

It is advantageous that the radial distribution of refractive optical power is divided into at least three functional zones that account for photopic, mesopic and scotopic vision.

Preferably the optical optimization of the aspherical shape is performed in order to minimize the sensitivity of the optical performance parameters with respect to a potential lens tilt induced by surgical effects or capsular bag symphysis.

Advantageously, the optical optimization of the aspherical shape is performed in order to minimize the sensitivity of the optical performance parameters with respect to a potential lens decentration induced by surgery effects or wound healing processes.

A preferred way of modeling and optimizing the lens shape includes selecting the radii of base curvature of the anterior and posterior surfaces as well as the central thickness, the edge thickness and the refractive index.

In the method according to the invention, the amount of spherical aberration of the artificial lens is maintained at the same level as that of the natural human lens over a broad range of pupil diameters.

Preferably the modified lens shape is defined in terms of a linear combination of polynomials.

The modified lens shape can be defined by the equation:

$$z = \frac{cr^2}{1+\sqrt{1-(1+Q)c^2r^2}} + k_2 r^2 + k_4 r^4 + k_6 r^6 + k_8 r^8$$

wherein:
$c = r_{curv}^{-1}$ (Curvature=1/base radius of curvature);
$r$=independent variable, radius about the optical axis;
$Q$=conic constant; and,
$k_n$=polynomial coefficient of order n.

In this way, the constant Q can be 0 or between −1 and 0. The coefficient $k_2$ can be equal to 0 and the coefficients $k_n$ for n>6 can be equal to 0.

Advantageously, the modified lens shape is defined in terms of a linear combination of polynomials or by splines or is piecewise defined by linear combinations of polynomials.

The optical performance can be defined as contrast according to contrast transfer function or definition brightness (Strehl ratio) or wavefront aberration or in terms of image point spread functions and encircled energy.

The aberrations of the entire optical system of the human eye can be expressed in linear combinations of Zernike or Seidel polynomials or as Fourier decomposition of the optical path length differences of the wavefront.

An aspheric intraocular lens according to the invention can be made of soft material or hydrophilic material (such as hydrophilic acrylic polymer or copolymer) or a hydrophobic material (such as hydrophobic acrylic or silicone).

The aspheric intraocular lens according to the invention can also be made of monobloc material with hard and soft zones such as described in European patent publication 1 003 446 or of hard material such as polymethylmethacrylate also known as PMMA.

In addition to correcting spherical vision errors, the surface modifications according to the invention allow the restoration of the optical properties of the natural human lens as they existed prior to extraction. Further, the intentional balancing of the anterior and posterior surface modulations provides a minimum sensitivity of the optical performance with regard to mechanical positioning disturbances, such as decentration and tilt of the IOL, which can be induced by surgery inaccuracy, surgical trauma or capsular bag symphysis.

This is achieved by intentional adjustment of the optical aberrations in a way to make them similar to the effects of the natural human crystalline lens.

The image formation in the natural human eye is accomplished by the combination of the ocular media and their boundary surfaces. The main contribution in refractive power (~75%) is provided by the cornea which forms the first air/media interface of the human eye. Rays emitted by distant object points enter the cornea almost parallel to the optical axis. The refraction of the cornea deflects the rays toward the optical axis and a converging bundle results. This bundle of rays passes the anterior chamber and enters the human crystalline lens. If no crystalline lens would be in place, the rays would converge to a single diffraction limited small spot at the distance of the inverse corneal refractive power. The spot size is determined by the diffraction effects at the periphery of the entrance pupil and the wavelength.

The optical system of the human eye is not perfect in terms of physics but it has developed and optimized over the ages. The slight aspherical shape of the cornea acts in conjunction with the non-linear Snell's law of refraction and prevents that all rays emitted from a distant point source converge at a single spot. It appears that rays from the outer regions of the pupil hit the optical axis at a shorter distance than the axial rays do. This effect is called spherical aberration (in the following abbreviated SA) and is provided with a sign. If the pupil peripheral rays hit the optical axis before the axial rays do, the SA is considered to be "positive". Positive spherical lenses show this behavior. If the pupil peripheral rays hit the optical axis at a more distant point than the axial rays, the SA is considered to be "negative". This behavior is found with planoparallel glass plates or negative lenses.

Since the peripheral rays of the cornea hit the optical axis before the axial rays do, the cornea adds positive SA to the optical system. This effect prevents the formation of infinitely sharp macular images. Instead, blurred spots result because there is much light diffusion. The evolution of the human eye accounted for this effect by developing a highly complex crystalline lens design. The crystalline lens contributes the missing 25% of refractive power to the optical system in order to adjust the focal length exactly to the available axial length of the human eye. In addition, the lens allows the accommodation to different viewing distances by internal adjustment of the refractive lens power. Beyond these obvious facts, the crystalline lens acts as an optical correction means of the human eye in that it compensates for optical errors introduced by the cornea. In order to avoid excessive spot blurring induced by the corneal positive SA, the crystalline lens provides a well adjusted amount of negative SA that almost completely compensates for the amount induced by the cornea. The optical performance of this combined optical system is significantly better than that of its individual components. This inherent compensation mechanism functions even for different viewing distances and different pupil diameters due to changing lighting conditions.

The main objective of the evolution of the human eye was not to optimize the theoretical optical performance of the eye in terms of image point spread functions or Strehl ratios as currently widely believed. Rather, the optical apparatus should provide an optical performance that accurately matches the requirements of the cone and rod structure of the retina, their local density functions and color perception properties. The mosaic of cones and rods permits only to see images with a maximum spatial frequency of 75 cpd; a higher spatial frequency can produce aliasing and distortion of the perceived image as described by Y. K. Nio et al in the article "Spherical and irregular aberrations are important for the optimal performance of the human eye", Ophthal. Physiol. Opt. 2002, 22, pages 103 to 112. The optical properties of the visual apparatus, the configuration of the retina and the physiological processing of the visual information in the visual cortex determine the perceivable visual acuity of the patient.

From the above, the main objectives of a novel intraocular lens can be derived. The inventors came to the conclusion that the IOL according to the invention has to restore both the optical power and the aberration characteristics of the natural human lens in order to support the neuro-visual optical system with respect to the best perceivable visual performance. For explanation, see, for example, the article of P. Artal et al entitled "Neural compensation for the eye's optical aberrations", Journal of Vision (2004), 4, pages 281 to 287.

The design of the novel intraocular lens takes into account the natural optical configuration of the human vision apparatus, for example, the visual axis tilt and the pupil decentration. In addition, the method accounts for potential positioning errors caused by implantation and surgery effects.

BRIEF DESCRIPTION OF THE DRAWINGS

The invention will now be described with reference to the drawings wherein.

The aspheric IOL according to the invention is referred to as "new aspherical IOL" in the graphs of FIGS. 3 and 6 to 13.

DESCRIPTION OF THE PREFERRED
EMBODIMENTS OF THE INVENTION

In order to provide a design environment for an IOL, a particular theoretical eye model needs to be applied. Many such models are well known from the literature, for example, Gullstrand: Helmholtz's Physiological Optics; Norrby et al.: "Methods of obtaining ophthalmic lenses providing the eye with reduced aberrations"; U.S. Pat. No. 6,609,793; or Thibos et al: "A new single surface eye that accurately predicts chromatic and spherical aberrations in the human eye", Invest. Ophthal. Visual Sci. 34, 777 (1993).

Figure 1:
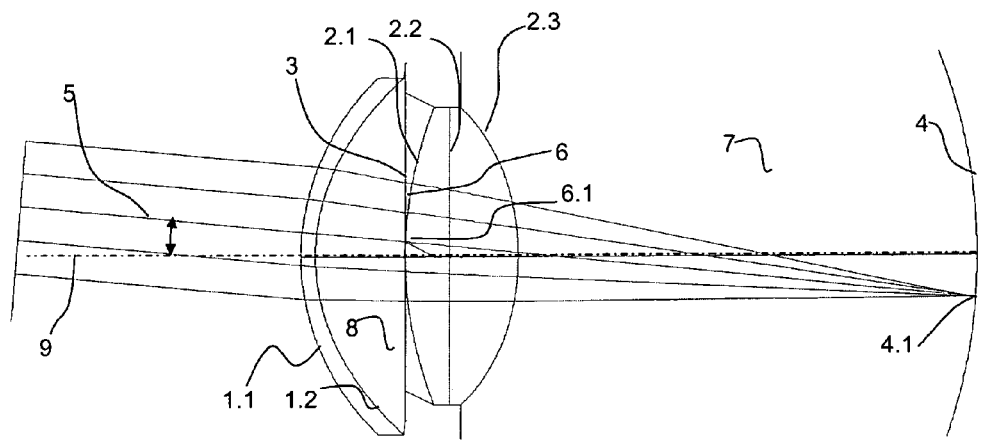
FIG. 1 shows the Liou-Brennan model eye with pupil decentration and visual axis tilt.
Figure 2:
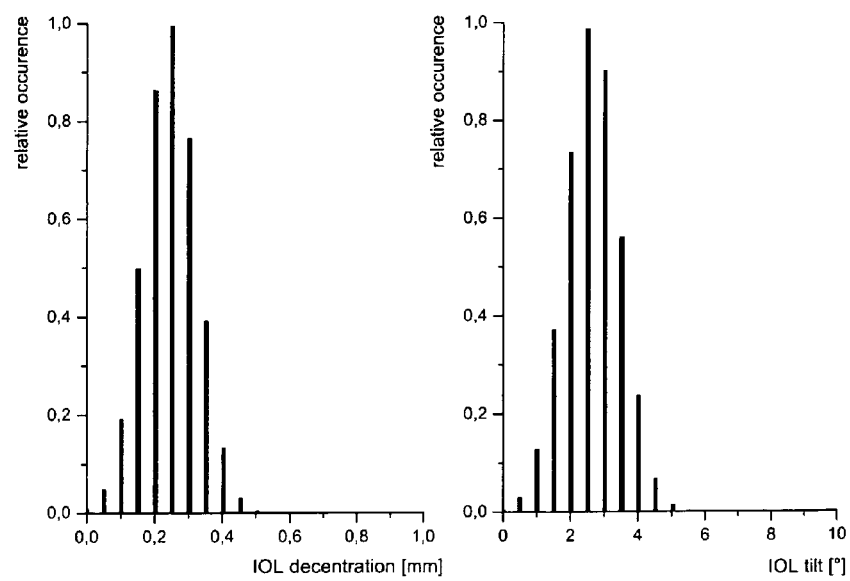
FIG. 2 shows the statistical distribution of IOL positioning errors.

All the above theoretical eye models as well as the majority of published eye models rely on simplified ocular configurations of the human eye. The cornea is reduced to a single surface element and the visual axis is assumed to match exactly the axis of symmetry of the eye. These reduced models try to duplicate the optical system and aberrations of the human visual apparatus by the use of single faced cornea models that apply some degree of asphericity in order to reflect the measurable performance. The authors proved that the above eye models comply with the measured results according to the given assumptions. However, these eye models disregard the specifics of the anatomy of the human eye in a more or less systematic way. The most comprehensive eye model currently available in literature was described by Liou and Brennan in the article "Anatomically accurate, finite model eye for optical modeling", J. Opt. Soc. Am. A, Vol. 14, No. 8, August 1997. The Liou-Brennan eye, as shown in FIG. 1, represents the ocular anatomy very closely and preserves the optical properties and aberration characteristics of the human eye. This eye model includes an aspherical cornea with anterior surface 1.1 and posterior surface 1.2 as well as an aspherical gradient-index lens model. The anterior chamber is identified by reference numeral 8, the vitreous body by 7 and the retina by 4. The model takes into account that, for the majority of the population, the visual axis 5 is tilted by 5° with respect to the axis of symmetry 9 of the eye in order to focus in the macular region 4.1. In addition, the pupil 6 is slightly decentered by 0.5 mm in nasal direction 6.1 for the majority of the population. The amount of spherical aberration (SA) is balanced by an aspheric cornea that introduces positive spherical aberration. An aspherical model of the natural lens, including two gradient-index components with optical surfaces (2.1, 2.2, 2.3), provides a negative SA to compensate for the corneal contribution. In total, the optical system provides a slight positive spherical aberration which is equivalent to the measured data and helps to increase the depth of focus. In contrast to other model eyes, the Liou-Brennan eye is therefore not rotationally symmetric.

The design of the novel artificial intraocular lenses uses an eye model that is based on the Liou-Brennan eye model as described by the listing of the surfaces:

| Surface | Comment | Radius | Thickness | Glass | Diameter | Conus |
|---|---|---|---|---|---|---|
| OBJ | — | Infinite | Infinite | — | 0 | 0 |
| 1 | — | Infinite | 1 | — | 4.495 | 0 |
| 2 | — | 0 | — | — | | |
| 3 | CORNEA_FRONT | 7.77 | 0.5 | CORNEA_LB | 12 | −0.18 |
| 4 | CORNEA_BACK | 6.4 | 3.16 | WATER_LB | 12 | −0.6 |
| 5 | PUPIL_DEC_1 | — | 0 | — | | |
| STO | PUPIL | Infinite | 0 | WATER_LB | 4 | 0 |
| 7 | PUPIL_DEC_2 | — | 0 | — | | |
| 8 | LENS_FRONT | 12.4 | 1.59 | — | 10 | −0.94 |
| 9 | LENS_CENTER | Infinite | 2.43 | — | 10 | 0 |
| 10 | LENS_BACK | −8.1 | 16.27 | WATER_LB | 10 | 0.96 |
| IMA | RETINA | −18 | | WATER_LB | 20 | 0 |

The invention is based on specific geometry and/or shape modifications which are applied to the anterior or posterior surface or to both surfaces of the novel intraocular lenses. The modified IOL surfaces include rotationally symmetric deviations from a spherical shape. This method is commonly understood as aspherization of optical surfaces. Since aspherical surfaces are already well known from the prior art, the following sections will explain the characteristics and improvements and will furthermore explain the differences to commonly known designs.

The new lens design is intended to improve the prior art in such a way that it provides a measurable improvement of the optical performance parameters that leads to a perceivable improvement of visual acuity and contrast vision performances for the patient. In order to do so, the disclosed lens design mimics the optical properties of the natural human lens under the conditions as described above in the Liou-Brennan eye model.

A substantial improvement of visual acuity is achieved by taking the statistics of potential lens displacements into account for the lens design. The shape of the IOL surfaces is optimized to minimize the sensitivity of the optical performance with regard to decentration and tilt of the implanted IOL. Different authors (Taketani et al: "Influence of intraocular lens optical design on higher-order aberrations", J. Cat. Refr. Surg., Vol. 31, May 2005) report a mean decentration of 0.1 mm to 0.25 mm as the most likely case with ranges up to 1 mm.

In addition, the new IOL design fulfills the boundary condition of keeping the natural spherical aberration at the same amount as the human crystalline lens for a broad range of pupil diameters. This allows the neurovisual system to adapt quickly to the new implant because the lifelong adaptation to the properties of the natural human eye does not need to be changed.

Figure 3:
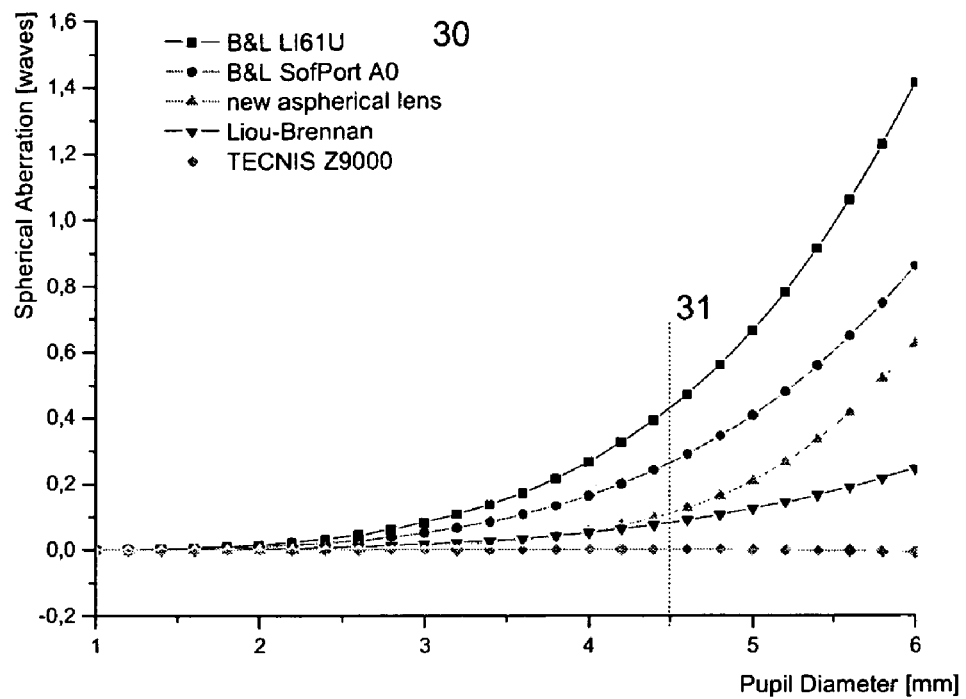
FIG. 3 shows the spherical aberration as a function of the pupil diameter for different IOLs.

FIG. 3 shows that the new aspherical IOL approach provides the least deviation from the characteristics of the natural human eye (Liou-Brennan). The orthonormal Zernike coefficients are computed using the notation defined in R. Noll, "Zernike polynomials and atmospheric turbulence", J. Opt. Soc. Am., Vol. 66, No. 3, p. 207 (1976). This is also known as the "Born-Wolf-notation" (Born, Wolf "Principles of Optics", Chapter 1). The amount of this particular aberration coefficient is expressed in waves (546 nm). The reference group consisting of several IOLs of the prior art (reference numeral 30) shows significantly larger differences of SA in pupil zones up to 4.5 mm (reference numeral 31) and above.

An aspherical shape that allows the above optical performance and capabilities can be described by the equation:

$$z = \frac{cr^2}{1+\sqrt{1-(1+Q)c^2r^2}} + k_2 r^2 + k_4 r^4 + k_6 r^6 + k_8 r^8 \quad (1)$$

wherein:

$c = r_{curv}^{-1}$ (curvature=1/base radius of curvature) 1)
$r$=independent variable, radius about optical axis
$Q$=conic constant
$k_n$=polynomial coefficient of order n.

Rotationally symmetric polynomial aspheric surfaces are described by a polynomial expansion of the deviation from a spherical surface (or an aspheric surface described by a conic section). The even aspherical surface model uses only the even powers of the radial coordinate to describe the asphericity. The model uses the base radius of curvature and the conic constant.

The coefficients of the polynomial expansion as well as the base radius are determined numerically in order to satisfy a least square fit to a particular merit function. This merit function accounts for the surgical statistics as described above and is minimized for optical performance. The merit function is represented by a set of different error and quality parameters that describe the desired optical performance. By definition, the optimal state of the optical system is reached at a global minimum of the merit function. In order to optimize the IOL surface shape to achieve the advantageous properties as disclosed, the merit function is constructed using weighted wavefront aberration operands, weighted MTF operands, localized optical power operands as well as boundary constraints such as center thickness and edge thickness.

The following set of coefficients describes a new aspherical IOL at a base power of 22 D (22 diopters).

| surface | $r_{curv}$ | Q | k2 | k4 | k6 | k8 |
|---|---|---|---|---|---|---|
| anterior | 7.1497 | 0.0 | 0.0 | 0.0 | 0.0 | 0.0 |
| posterior | −36.3903 | 0.0 | −6.8159E−003 | 1.0213E−003 | −6.2142E−005 | 0.0 |

In accordance with equation (1), the required range of base optical powers from 5 D to 40 D can be easily calculated by setting the localized target power operands of the merit function to the desired power values and minimizing the remaining errors accordingly.

Figure 4:
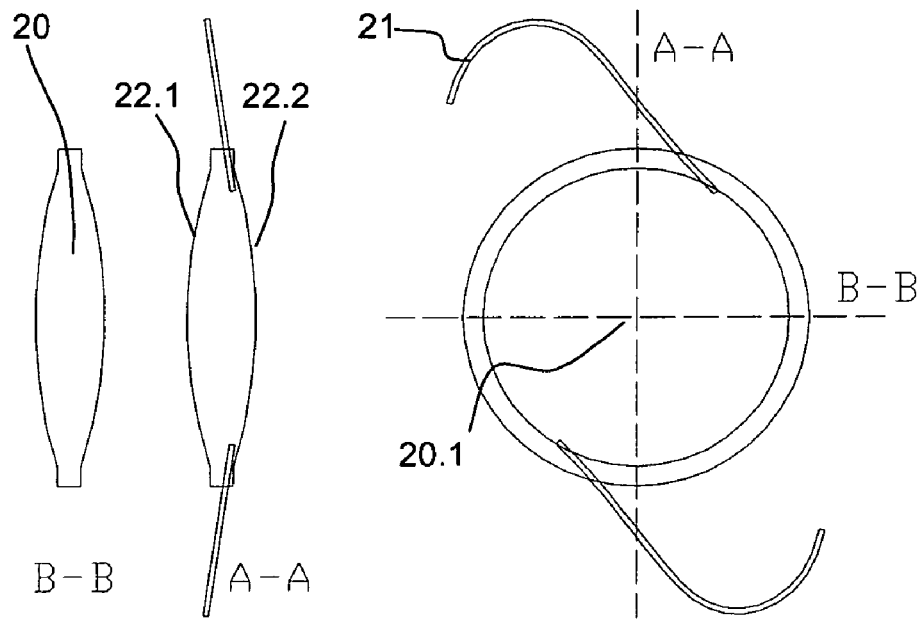
FIG. 4 shows the layout of the aspherical IOL according to the invention.
Figure 5:
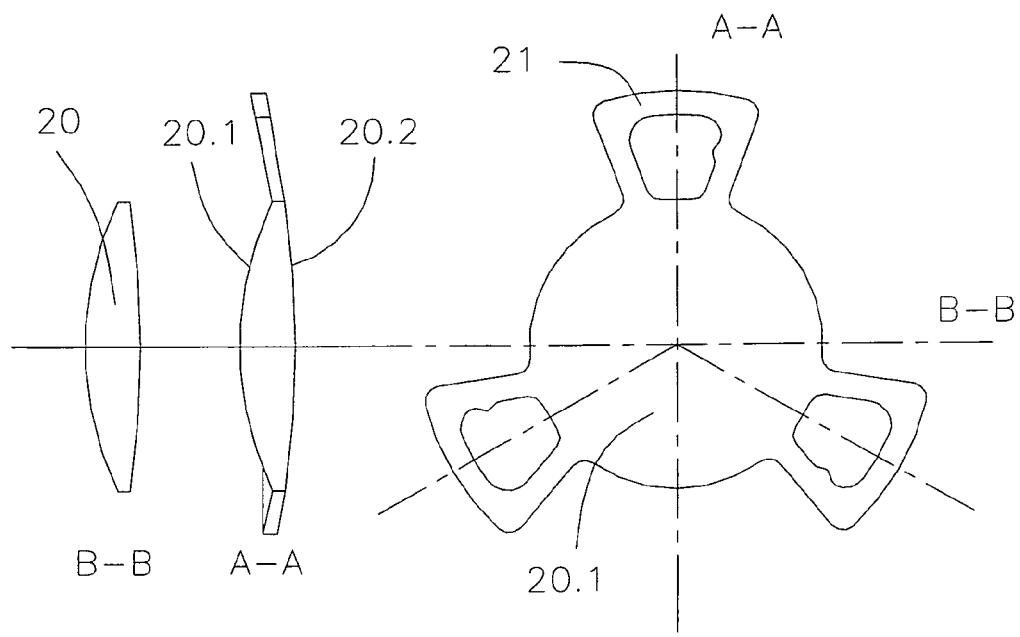
FIG. 5 shows another embodiment of the aspherical IOL according to the invention.

An example of a possible layout can be seen in FIG. 4. The lens can be made of three parts but this is not a requirement. Other preferred embodiments include 2-part configurations or single part IOLs as presented in FIG. 5. Reference numeral 20 refers to the IOL body or the bulk material of the IOL; 21 is the haptics mechanism; and, 20.1 is the optically effective zone of the IOL. At least one of the optical surfaces 22.1 and 22.2 is aspherical. In the example described above, surface 22.2 is aspherical.

Figure 6:
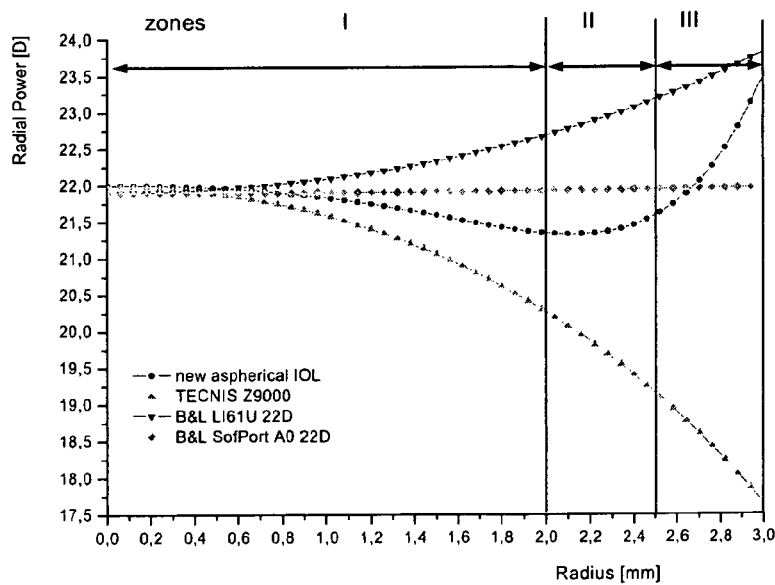
FIG. 6 shows the radial optical power and corresponding zones for different IOLs.

FIG. 6 shows the radial refractive power profile of the modified IOL in comparison with other lens designs of the prior art. The enhanced capabilities result from the particular characteristic of the radial refractive power distribution as a function of the radius normal to the optical axis. All IOLs start at their paraxial refractive power of 22 D (22 diopters) at a radius of 0 mm. The refractive power of the symmetric biconvex lens B&L LI61 increases continuously toward the lens edge. This indicates a significant amount of SA that exceeds the naturally given amount. In contrast, the optical power of the lens TECNIS Z9000 decreases greatly with increasing radius to provide a negative SA that compensates for the corneal contribution. The drawback of this approach results from the high sensitivity of this design with regard to a decentration of the IOL. The third example of the prior art is the "aberration free IOL" B&L SofPort A0. This lens assumes independence of the optical performance with respect to decentration. This is accomplished by keeping the radial power at a value equal to the paraxial power for all radii. In this case the lens is free from an inherent SA. If this condition is satisfied, a decentration does not cause coma errors which compromise image quality dramatically in the presence of decentration. Despite the mentioned advantages, this lens design has a significant disadvantage. The natural compensation effect of the human crystalline lens is completely ignored. The image quality at the retina is therefore suboptimal for the patient since the full amount of the corneal SA affects the visual acuity in a negative way.

FIG. 6 shows how the new IOL resolves the problems of the known IOL designs of the prior art. The distribution of the optical power as a function of lens radius is selected in different zones so that an optimal performance is achieved which is perceived by the patient.

In zone I, the optical power decreases continuously and smoothly in a pupil region starting from radius 0 mm through 2.0 mm. This pupil region is most active for photopic vision under bright light conditions. The compensation for the corneal SA allows a diffraction limited performance and an improved contrast vision. In the zone II, a pupil region from r=2.0 mm through r=2.5 mm, the optical power is less than that of the paraxial region in order to compensate for corneal SA at large pupils under mesopic conditions. The increase in optical power from r=2.5 mm to r=3 mm in zone III reduces the sensitivity of the modulation transfer function with respect to decentration and tilt.

Figure 7:
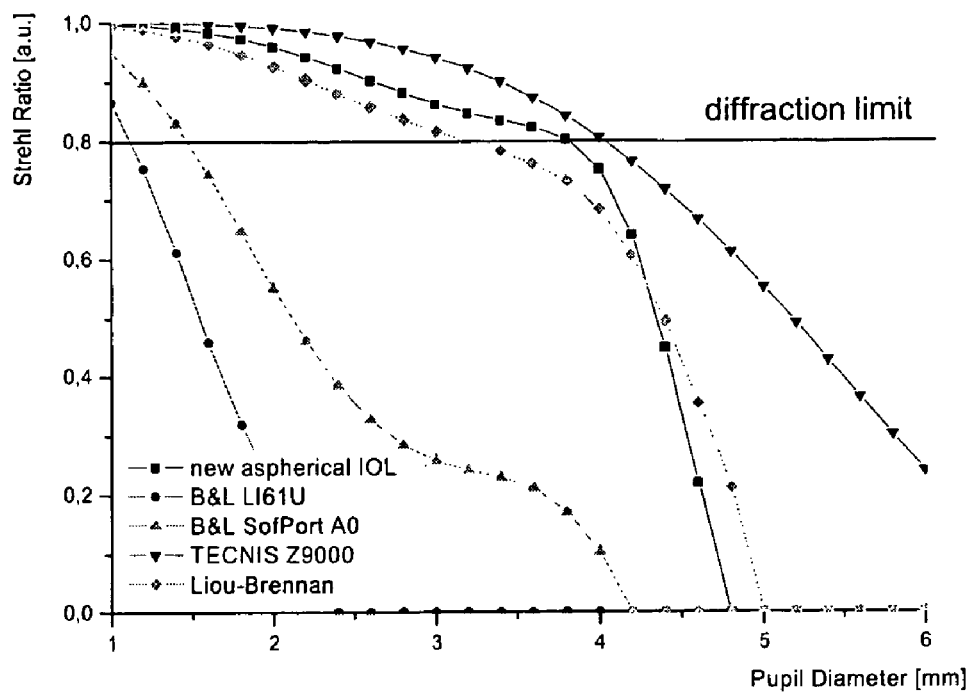
FIG. 7 shows Strehl ratio as a function of pupil diameter for different IOLs; and, FIGS. 8 to 13 show modulation transfer functions for different IOLs for different pupil diameters, decentrations and tilt angles.

FIG. 7 shows that the new lens design ensures a diffraction limited performance up to a pupil size of 4 mm and equals the performance (Strehl ratio as a function of pupil diameter) of the natural crystalline lens for the entire pupil range.

Figure 8:
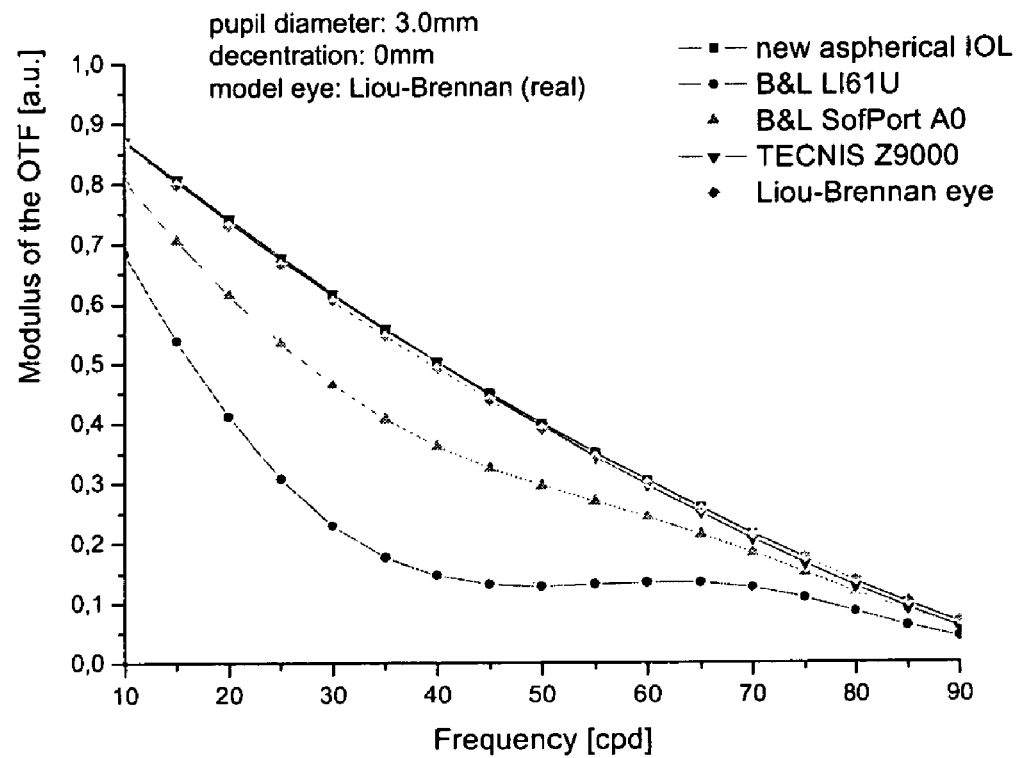

Further, the new lens design equals the diffraction limited optical performance (MTF) of the best prior art designs in case of physical pupil diameters of 3 mm at no decentration (see FIG. 8).

Figure 9:
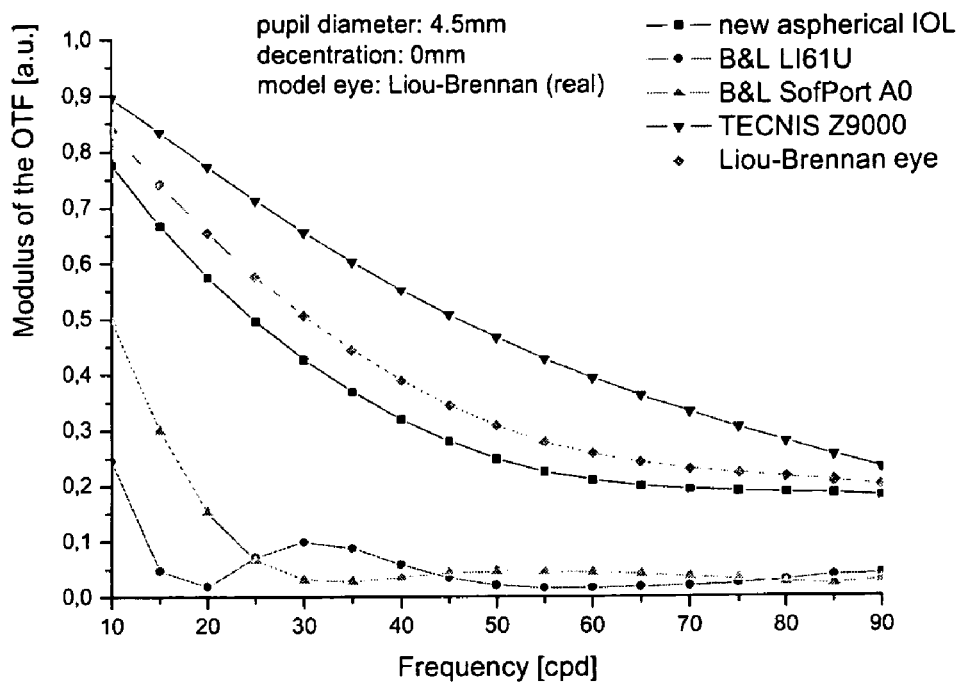

FIG. 9 shows that the new IOL equals the optical performance (MTF) of the natural human eye in case of physical pupil diameters up to 4.5 mm at no decentration.

Figure 10:
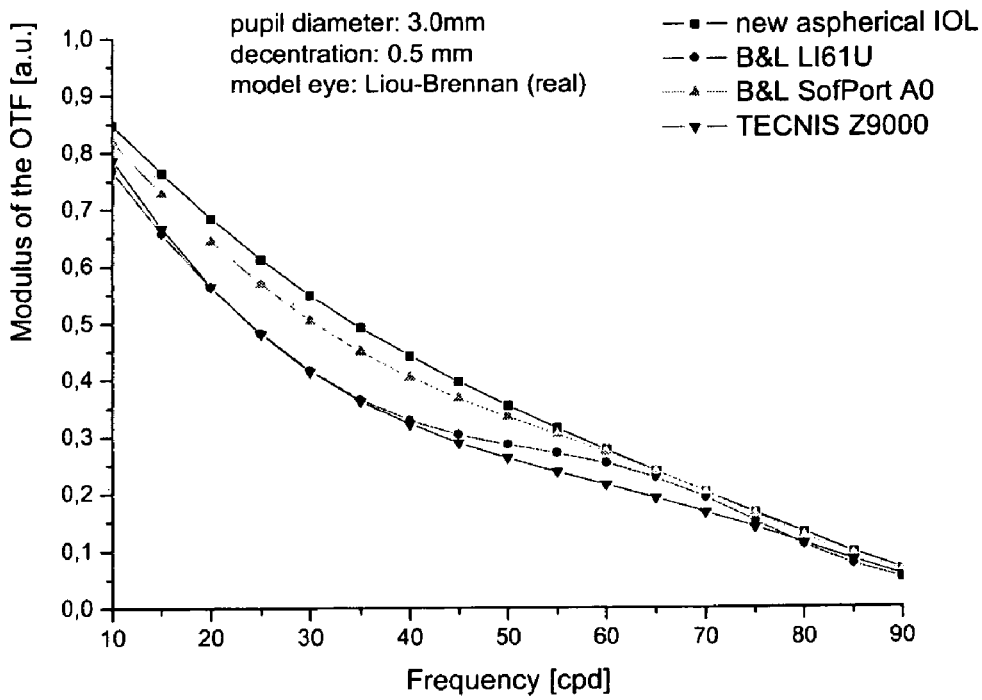
Figure 11:
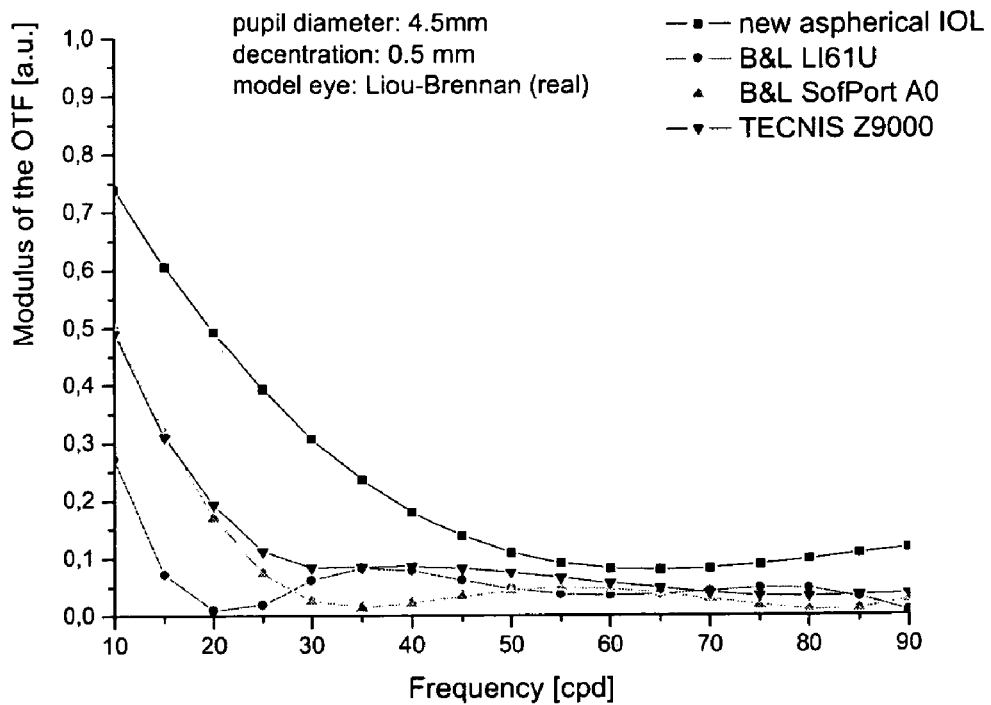
Figure 12:
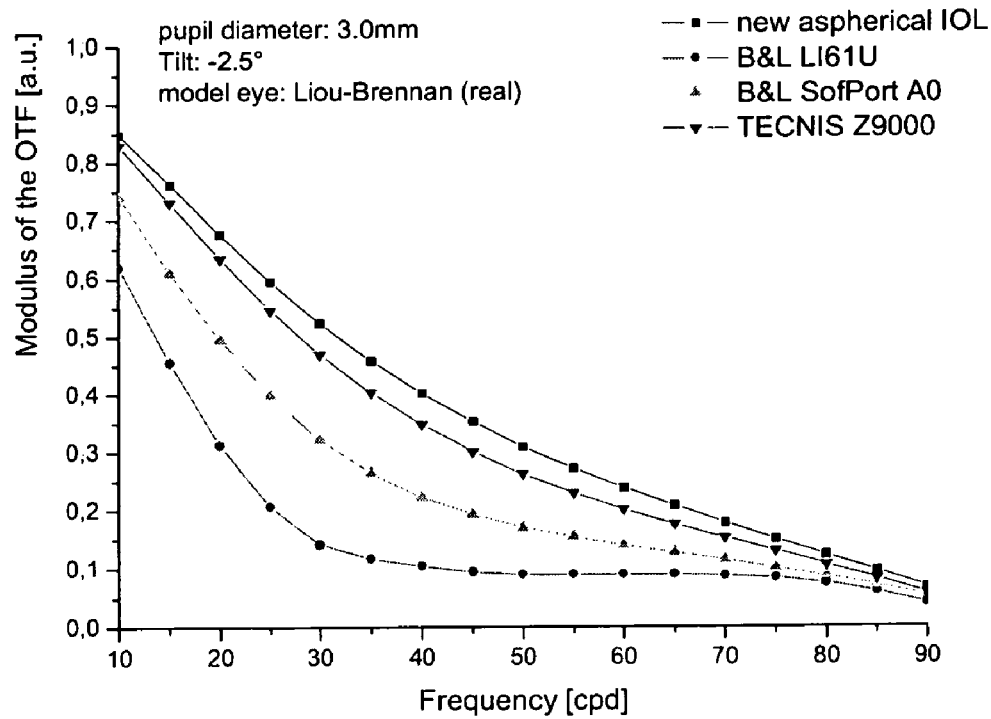
Figure 13:
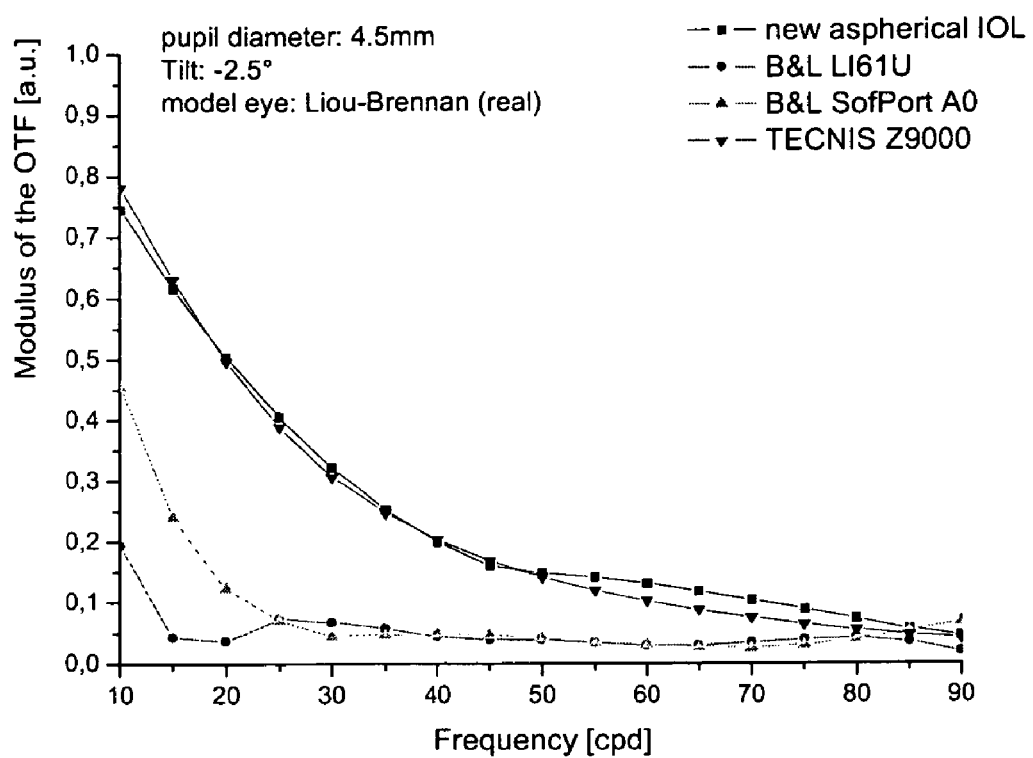

FIGS. 10 and 11 show a significantly reduced sensitivity of the optical performance (MTF) with respect to decentration, while FIGS. 12 and 13 show that the same is true with respect to tilt.

It is understood that the foregoing description is that of the preferred embodiments of the invention and that various changes and modifications may be made thereto without departing from the spirit and scope of the invention as defined in the appended claims.

What is claimed is:

1. A method for making an intraocular lens capable of adjusting the aberrations of the eye in order to provide optimal vision correction to patients, the method comprising the steps of: providing a mathematical model eye that describes the optical setup and performance of the natural human eye including a visual axis tilted with respect to the axis of symmetry of the eye; and, a decentered iris that represents a decentered entrance pupil; determining the performances of the mathematical model eye with respect to image quality and spherical aberrations as a function of pupil diameter; using a mathematical model describing the statistics of potential lens misalignments and positioning errors induced by surgery or wound healing processes; calculating the optical performance and resulting aberrations employing said mathematical eye model convoluted with the statistical model for lens displacements; and, optically modeling an aspherical lens shape that replaces 20 the natural human crystalline lens in the eye that provides optical power restoration while providing optical characteristics of the human lens in order to cause the eye with the intraocular lens having aspherical shape to have the same amount of spherical aberrations and the same level of image quality than the mathematical model eye as a function of the pupil diameter; and, producing the intraocular lens based on the data acquired by the above method steps.

2. The method of claim 1, wherein the radial distribution of refractive optical power is divided in at least three functional zones that account for photopic, mesopic and scotopic vision.

3. The method of claim 1, wherein modeling and optimization of the lens shape includes selecting the radii of base curvature of the anterior and posterior surfaces as well as the central thickness, the edge thickness and the refractive index.

4. The method of claim 1, wherein the amount of spherical aberration of a mathematical model eye having the intraocular lens is maintained at the same level as the mathematical model eye having a human crystalline lens for pupil diameters ranging from greater than 0 to 4 mm.

5. The method of claim 1, wherein the modified lens shape is defined in terms of a linear combination of polynomials.

6. The method of claim 1, wherein the modified lens shape is defined by the equation:

$$z = \frac{cr^2}{1 + \sqrt{1-(1+Q)c^2r^2}} + k_2 r^2 + k_4 r^4 + k_6 r^6 + k_8 r^8$$

wherein:

$c = r_{curv}^{-1}$ (curvature=1/base radius of curvature)

r=independent variable, radius about optical axis

Q=conic constant $k_n$=polynomial coefficient of order n.

7. The method of claim 6, wherein $k_2$ is 0.

8. The method of claim 1, wherein said mathematical model eye that describes the optical setup and performance of the natural human eye further includes an aspherical corneal surface, a gradient index and an aspherical crystalline lens model.

9. The method of claim 1, wherein said mathematical model eye that describes the optical setup and performance of the natural human eye further includes an aspherical corneal surface.

10. The method of claim 1, wherein said mathematical model eye that describes the optical setup and performance of the natural human eye further includes a gradient index.

11. The method of claim 1, wherein said mathematical model eye that describes the optical setup and performance of the natural human eye further includes an aspherical crystalline lens model.

12. The method of claim 1, wherein said mathematical model eye that describes the optical setup and performance of the natural human eye further includes an aspherical corneal surface and a gradient index.

13. The method of claim 1, wherein said mathematical model eye that describes the optical setup and performance of the natural human eye further includes a gradient index and an aspherical crystalline lens model.

14. The method of claim 1, wherein said mathematical model eye that describes the optical setup and performance of the natural human eye further includes an aspherical corneal surface and an aspherical crystalline lens model.

* * * * *

UNITED STATES PATENT AND TRADEMARK OFFICE
CERTIFICATE OF CORRECTION

PATENT NO. : 8,235,525 B2
APPLICATION NO. : 13/064073
DATED : August 7, 2012
INVENTOR(S) : Cédric Lesage and Mario Gerlach Page 1 of 1

It is certified that error appears in the above-identified patent and that said Letters Patent is hereby corrected as shown below:

In Column 2:
Line 17: delete "29000)" and substitute -- Z9000) -- therefor.
Line 28: delete "29000" and substitute -- Z9000 -- therefor.

In Column 8:
Line 43: delete "1)" after -- curvature) --.

In Column 10, claim 1:
Line 48: delete "20" after -- replaces --.

Signed and Sealed this
Second Day of October, 2012

David J. Kappos
*Director of the United States Patent and Trademark Office*